US00PP23801P3

(12) United States Plant Patent
Higaki

(10) Patent No.: US PP23,801 P3
(45) Date of Patent: Aug. 6, 2013

(54) *HYDRANGEA* PLANT NAMED 'BC7.14'

(50) Latin Name: ***Hydrangea macrophylla* (Thunb.)**
Varietal Denomination: BC7.14

(75) Inventor: Harrison M. Higaki, San Mateo, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 79 days.

(21) Appl. No.: 13/135,034

(22) Filed: Jun. 23, 2011

(65) Prior Publication Data

US 2012/0331601 P1 Dec. 27, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

U.S. PATENT DOCUMENTS

PP10,928 P * 6/1999 Rampp et al. ..... Plt./250
PP21,291 P3 * 9/2010 Meinl ..... Plt./250
PP21,796 P3 * 3/2011 Rampp ..... Plt./250

* cited by examiner

*Primary Examiner* — June Hwu
(74) *Attorney, Agent, or Firm* — James R. Cypher; Charles R. Cypher

(57) ABSTRACT

A new and distinct cultivar of *Hydrangea macrophylla* (Thunb.) named 'BC7.14' originated as a controlled cross between varieties. The cultivar 'BC7.14' can be blue or red depending on the acidity of the soil and the presence of aluminum. The variety 'BC7.14' has relatively compact, attractive inflorescences with relatively small sepalous florets, distinct sepal pigmentation and good commercial characteristics. When grown in the presence of aluminum, the upperside of the sepals is primarily R.H.S. 94 A (violet-blue group) and 86 B (violet group), the underside of the sepals is R.H.S. 93 D (violet-blue group) and 86 C violet group).

3 Drawing Sheets

Botanical classification: *Hydrangea macrophylla* (Thunb.) 'BC7.14'.

Variety denomination: 'BC7.14'.

BACKGROUND OF THE INVENTION

This invention relates to a new and distinct cultivar of the Saxifragaceae family. The botanical name of the plant is *Hydrangea macrophylla* (Thunb.) 'BC7.14'.

The new cultivar originated as a seedling from a controlled cross between a commercial variety known as 'Venedig' to the inventor which may be the subject of U.S. Plant Pat. No. 10,928 and registered as 'Venice Raven'. 'Venedig' was the seed parent and the unpatented variety 'LK49' was the pollen parent. 'LK49' is relatively compact plant with wiry stems, relatively small leaves, relatively small sepalous florets, and inflorescences that are resistant to being damaged by conditions in commercial coolers.

The variety 'BC7.14' has compact, attractive inflorescences with relatively small sepalous florets, attractive sepal pigmentation and good commercial characteristics. The variety 'BC7.14' has pigmented sepals, and is preferably grown in soil conditions treated with aluminum to produce blue pigmentation. The color of the sepals changes as the plant ages. Below is a table comparing the new variety to similar varieties.

TABLE 1

| | New Variety 'BC7.14' | Currently patent Pending Variety 'BC6.1' 13/135,028 | U.S. Plant Pat. No. 18,593 'True Blue' | Commerical variety 'Venedig' which may be U.S. Plant Pat. No. 10,928 'Venice Raven' |
|---|---|---|---|---|
| Leaf size | 8 cm × 13.5 cm | 12 cm wide × 15 cm long | Unknown | 11 cm wide × 15.5 cm long-source U.S. Plant Pat. No. 10,928 |
| Plant height | 14" in 6" pot. | 15" in 6" pot. | Unknown | 12" in 6" pot-observed controls grown alongside new variety. |
| Stem strength | Strong | Stems are strong but benefit from being staked | Strong | Strong-observed controls grown alongside new variety |
| Sepal Pigmentation | Upper side of sepals is R.H.S. 94 A (violet-blue group) to 86 B (violet group); Under side of sepals is R.H.S. 93 D (violet group) to 86 C (violet group). | Upper side of sepals is R.H.S. 86 A (violet group); Under side of sepals is R.H.S. 88 D (violet group) | Both sides of sepalsa are R.H.S. 100 D (blue group). | Upper side of sepals is R.H.S. 84 A (violet group). Under side of sepals is R.H.S. 85 A (violet group) observed controls grown alongside new variety. |

TABLE 1-continued

| | New Variety 'BC7.14' | Currently patent Pending Variety 'BC6.1' 13/135,028 | U.S. Plant Pat. No. 18,593 'True Blue' | Commerical variety 'Venedig' which may be U.S. Plant Pat. No. 10,928 'Venice Raven' |
|---|---|---|---|---|
| Sepalous Floret Size | 50 mm | 60 mm to 70 mm | 50 mm to 60 mm | 70 mm-observed controls grown alongside new variety |

The new cultivar 'BC7.14' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BC7.14' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
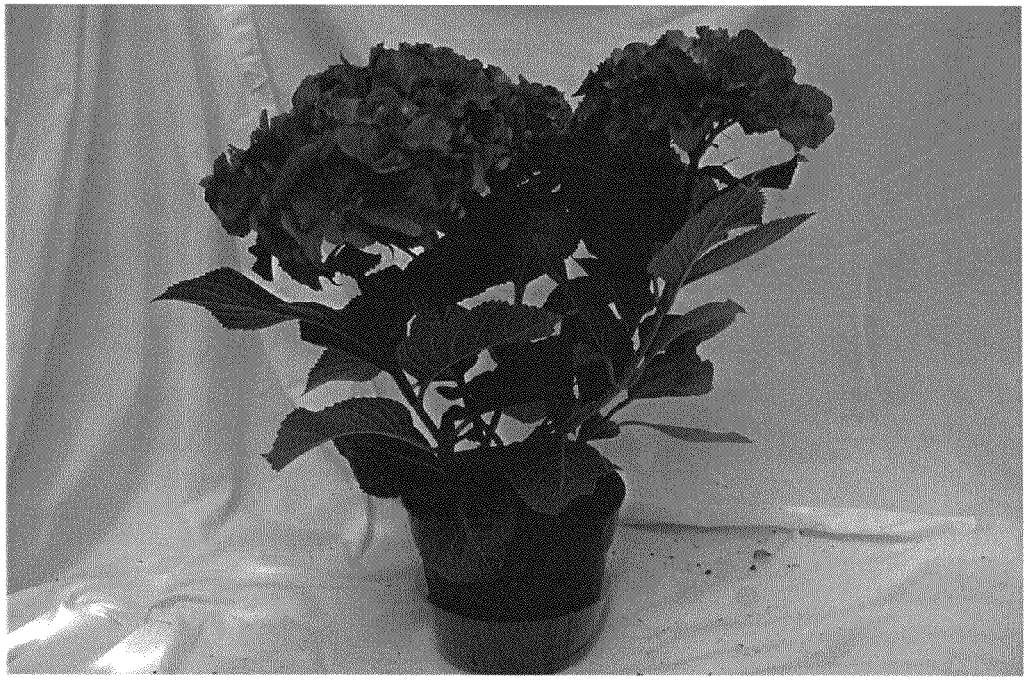
FIG. 1 is a view of the entire plant showing its form, growth habit, dark green foliage, inflorescence, and the color of its sepals.
Figure 2:
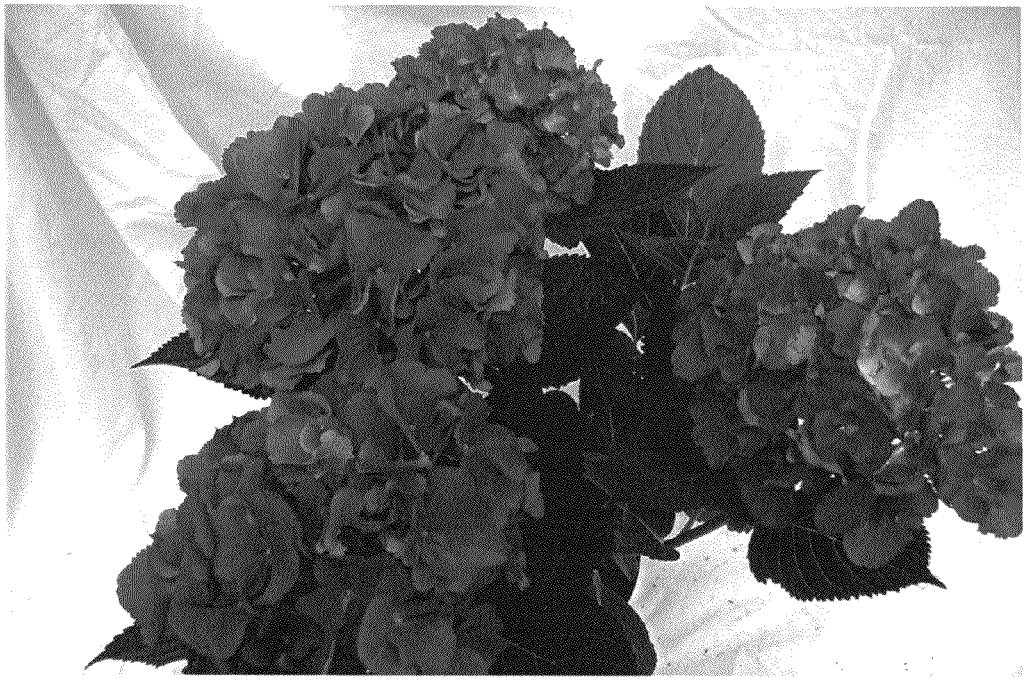
FIG. 2 is a view of the entire plant showing its form, growth habit, dark green foliage, inflorescence, and the color of its sepals.
Figure 3:
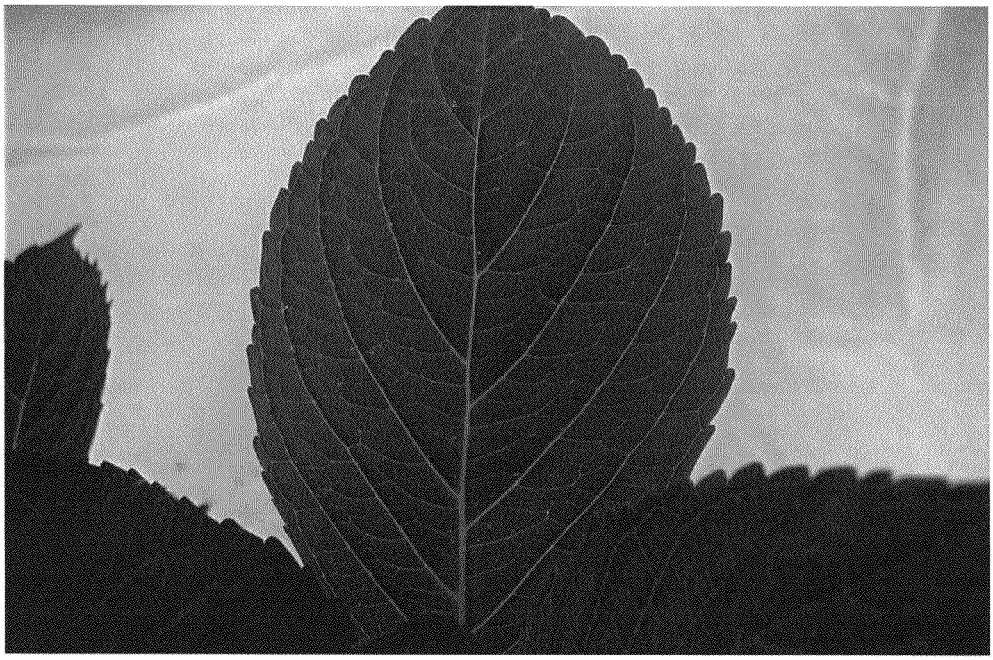
FIG. 3 is a close-up view of the adaxial surface of a mature leaf.
Figure 4:
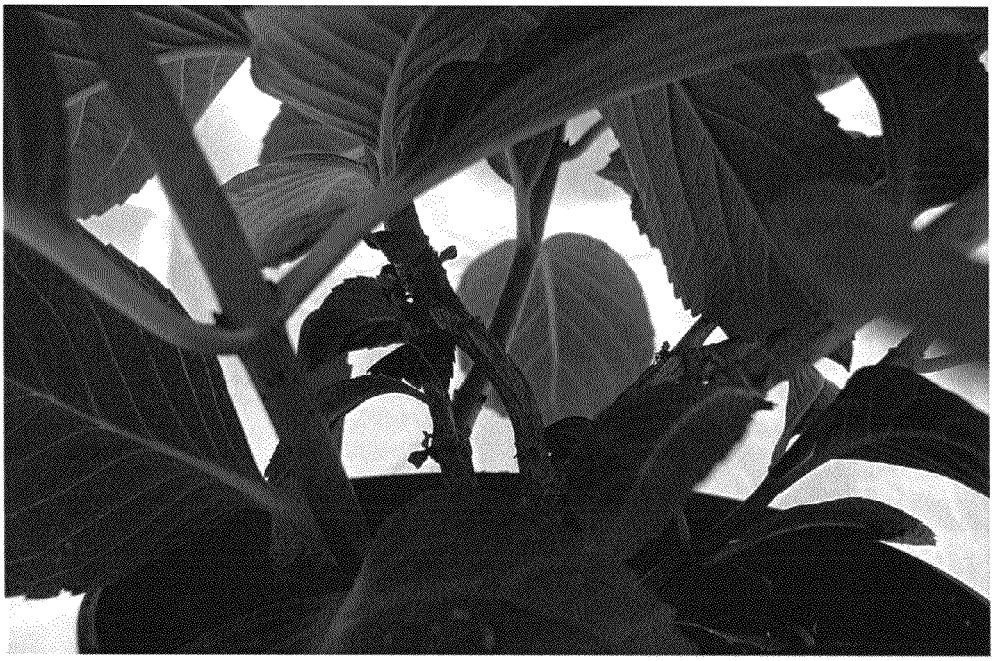
FIG. 4 is a close-up view of the base of the stem.
Figure 5:
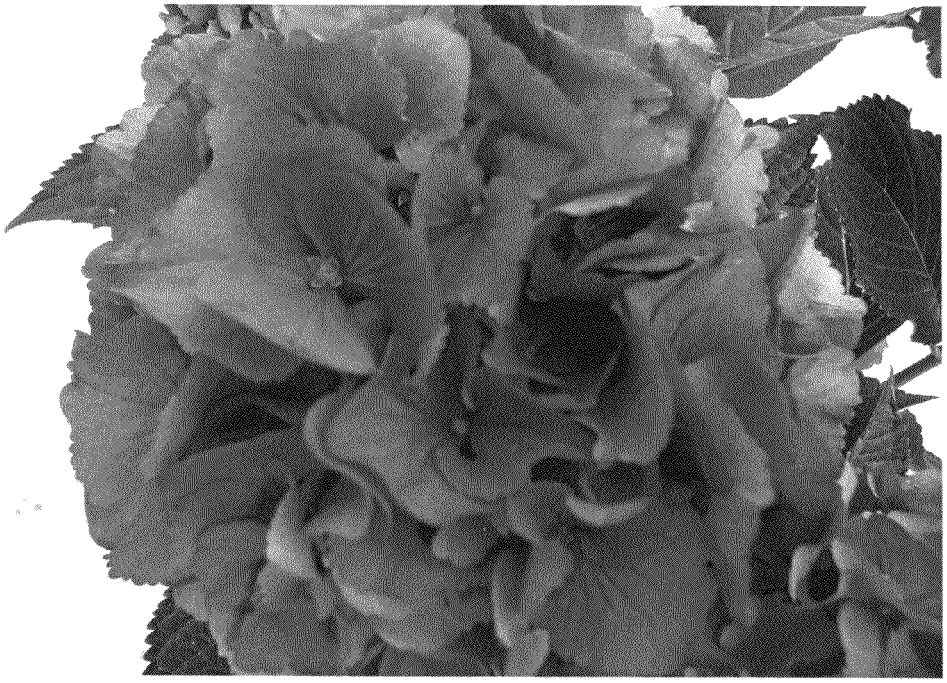
FIG. 5 is a close-up view of the upperside of a panicle of the new variety.
Figure 6:
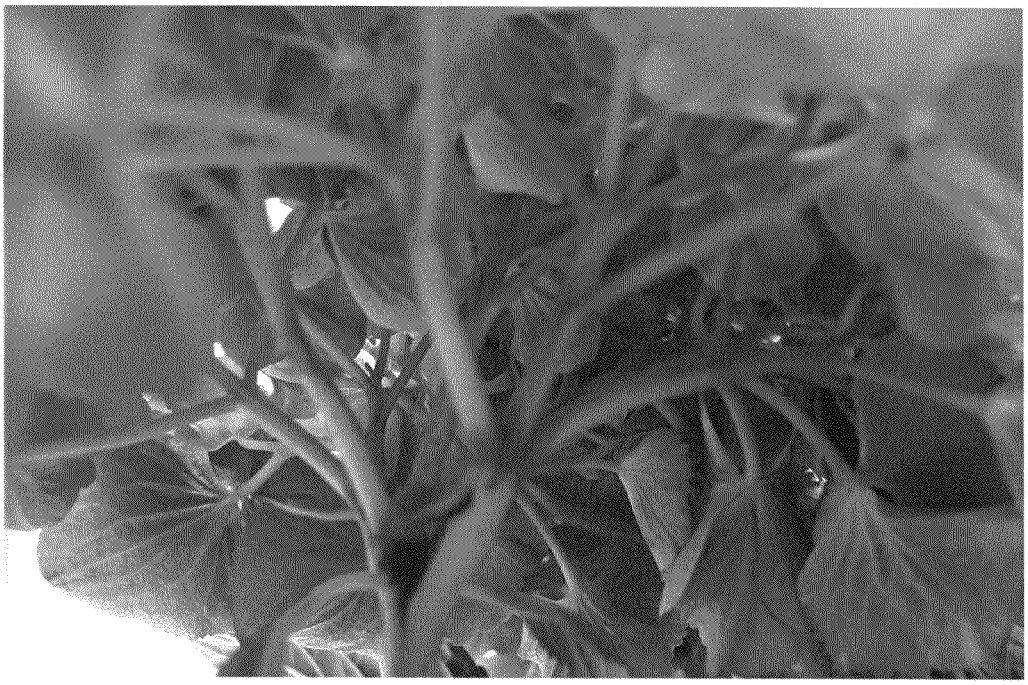
FIG. 6 is a close-up view of the center of a panicle of the new variety.

The plants shown in the figures are approximately 46 weeks old. The plant started out as cuttings, taken from the stem of a grown plant. The cuttings were placed in a pot and the soil was periodically treated with aluminum to produce blue pigmentation. The plant was pinched early to promote lateral branches.

'BC7.14' has not been observed under all possible environmental conditions. The phenotype may vary significantly with variations in environment such as temperature, light intensity and day length. Color determinations were made with The Royal Horticultural Society (R.H.S.) Colour Chart, in association with the Flower Council of Holland, located in Lieden.

THE PLANT

Origin: Controlled cross. The new cultivar originated as a seedling from a controlled cross between the commercial variety known to the inventor as 'Venedig' and which may be 'Venice Raven', U.S. Plant Pat. No. 10,928, which was the seed parent and the unpatented variety 'LK49' which was the pollen parent.

Form: Upright, compact shrub. A typical plant with a mature inflorescence that is ready for sale is approximately 14" high and has a diameter of 18" when grown in a 6" pot with appropriate soil amendments.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 2 mm long. The surface of young stems is glabrous. Stems become woody as they age. The color of typical young stems and young lateral branches is R.H.S. 144 A (green group). The older portions of the stems are R.H.S. 199 A (grey-brown group) Younger portions of the stems are 5 to 7 mm in diameter. Older portions of the stems are 5 to 7 mm in diameter.

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the upper leaf surface.

*Color.*—Mature leaves have an upper side that is R.H.S. 147 A (yellow-green group), and an under side that is R.H.S. 138 B (green group). Leaves are pinnately veined. The midvein and veins branching off the midvein are large and prominent on the underside of the leaves. Veins are R.H.S. 144 D (yellow-green group). Leaves are as wide as 8 cm and 13.5 cm long. Petioles are smooth and 2.0-2.5 cm long and 4 mm wide. Petioles are R.H.S. 144 D (yellow-green group).

BUDS

Form: Globose with 4 to 5 connate, elliptic, smooth petals. Most buds, whether they will mature into sepalous or non-sepalous florets, have 4 petals. Buds in the center of the inflorescence are non-sepalous. The majority of buds will develop into sepalous florets. They are approximately 1 mm by 1 mm when very young. Buds can be 3 mm in diameter and still unopened. Color of buds is R.H.S. 100 C (blue group).

Aspect: Smooth.

Arrangement: Borne on branched panicles.

INFLORESCENCE

Form: Paniculate. Terminal. As many as 100 individual flowers (florets) per inflorescence. Both sepalous florets and non-sepalous florets borne on same panicle. Flowers do not produce a fragrance. The peduncle for the inflorescence is strong and upright. Very few non-sepalous florets developing early on cymes that are later hidden by sepalous florets. Florets, both sepalous and non-sepalous, have anthers and style. Inflorescences are long-lasting, up to six weeks.

Size of inflorescence: Compact and globose. Individual inflorescence size is dependent on the number of florets. A typical inflorescence can grow as large as 6" in diameter, and 4" high.

Shape: Clusters of numerous small florets; sepalous florets overlap one another. Sepals are persistent.

Appearance: Showy.

FLORETS

General: The non-sepalous florets at the center of the inflorescence open first. Sepalous and non-sepalous florets are perfect and complete.

*Corolla*.—Generally, for both sepalous and non-sepalous florets there are 4 petals which fall off as flower matures. Petals are typically 4 mm long and 3 mm wide. Pedicel length for non-sepalous florets averages 4 mm. Pedicel length of sepalous florets is approximately 20 mm in length for plants of this age. Pedicels of both sepalous and non-sepalous florets continue to elongate as the inflorescence ages. Pedicel of both sepalous and non-sepalous florets are primarily 97 A (violet-blue group) and 95 C (violet-purple group).

Stamens: 8 stamens. Pollen is R.H.S. 158 C (yellow-white group). Plant produces abundant pollen. Filament is approximately 3 mm long. Filament is R.H.S. 155 C (white group). Anther is 1 mm long and is regular and basally attached.

Stigma: Two to three style each, although most florets have two style. Each style has one stigma. Style is typically 1 mm long. Style is R.H.S. 155 D (white group). Stigma is R.H.S. 155 D (white group).

Ovary: Ovary is partially inferior.

Sepalous florets:

*General*.—Veins dominate on the underside of the sepals.

*Number of sepals*.—4 or 5 sepals per floret, usually 4.

*Aspect of sepals*.—Smooth and glaucescent.

*Shape of sepals*.—Reniform with acuminate apex. Edges are entire, but with some crenation.

*Size of sepals*.—As the florets mature, the sepals enlarge and overlap each other more and more, until, often, there is no space between the sepals when the petals of the florets open. Sepals at maturity are typically 3.0 cm long and 4.0 cm wide. Flowers are typically 5 cm in diameter. The upper sides of the sepals are primarily R.H.S. 94 A (violet-blue group) and 86 B (violet group) and the under sides are primarily R.H.S. 93 D (violet-blue group) and R.H.S. 86 C (violet group). Blue pigmentation develops at the tips of the sepals and travels inward towards the base of the sepals.

Fruit: None.

Disease and pest resistance: Unknown.

I claim:

1. A new and distinct *Hydrangea macrophylla* plant named 'BC7.14' substantially as herein shown and described.

* * * * *